(12) United States Patent
Douglas et al.

(10) Patent No.: US 7,464,605 B2
(45) Date of Patent: Dec. 16, 2008

(54) BED HAVING A PATIENT POSITION MONITORING SYSTEM

(75) Inventors: Stephen L. Douglas, Batesville, IN (US); James R. Stolpmann, Lawrenceburg, IN (US); Terry L. Richter, Cincinnati, OH (US); Glenn C. Suttman, Batesville, IN (US); Kenith W. Chambers, Batesville, IN (US); Andrew F. Skinner, Batesville, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 504 days.

(21) Appl. No.: 11/221,217

(22) Filed: Sep. 7, 2005

(65) Prior Publication Data

US 2006/0070456 A1 Apr. 6, 2006

Related U.S. Application Data

(60) Provisional application No. 60/608,012, filed on Sep. 8, 2004.

(51) Int. Cl.
*G01L 3/00* (2006.01)
(52) U.S. Cl. ............................................. 73/795
(58) Field of Classification Search ............ 73/705–856
See application file for complete search history.

(56) References Cited

U.S. PATENT DOCUMENTS

| 4,179,692 | A | | 12/1979 | Vance |
| 4,624,784 | A | * | 11/1986 | Lefebvre .............. 210/321.67 |
| 4,633,175 | A | * | 12/1986 | Ritchie et al. ............... 324/760 |
| 4,800,973 | A | * | 1/1989 | Angel ....................... 177/211 |
| 4,814,661 | A | * | 3/1989 | Ratzlaff et al. .............. 310/328 |
| 5,253,656 | A | | 10/1993 | Rincoe et al. |
| 5,353,012 | A | | 10/1994 | Barham et al. |
| 5,515,044 | A | | 5/1996 | Glatt |
| 5,808,552 | A | | 9/1998 | Wiley et al. |
| 5,823,278 | A | * | 10/1998 | Geringer ..................... 177/144 |
| 6,067,019 | A | | 5/2000 | Scott |
| 6,161,891 | A | * | 12/2000 | Blakesley ................. 296/65.01 |
| 6,208,250 | B1 | | 3/2001 | Dixon et al. |
| 2002/0080037 | A1 | | 6/2002 | Dixon et al. |

OTHER PUBLICATIONS

State-of-the-Art Pointing Solutions for the OEM, FSR® Force Sensing Resistor® Integration Guide and Evaluation Parts Catalog, 400 Series Evaluation Parts with Suggested Electrical Interfaces, Versa Point Technology, Interlink Electronics, pp. 5-25, http://www.interlinkelectronics.com.
High Performance Foams, Rogers Corporation, pp. 1-2, http://www.rogers-corp.com/hpf/CT/Poron-I/aboutporon.htm, pp. 1-2, 2004.
FSR® Force Sensing Resistors®, Interlink Electronics.
Force Sensing Resistors, Frequently Asked Questions, Force Sensing Resistors from Interlink Electronics, FAQs, http://www.interlinkelec.com/support/faqs/page11.htm, , p. 1, 2004.

* cited by examiner

*Primary Examiner*—Max Noori
(74) *Attorney, Agent, or Firm*—Barnes & Thornburg LLP

(57) ABSTRACT

A patient sensor configured to detect the presence of a patient on a patient support surface.

21 Claims, 6 Drawing Sheets

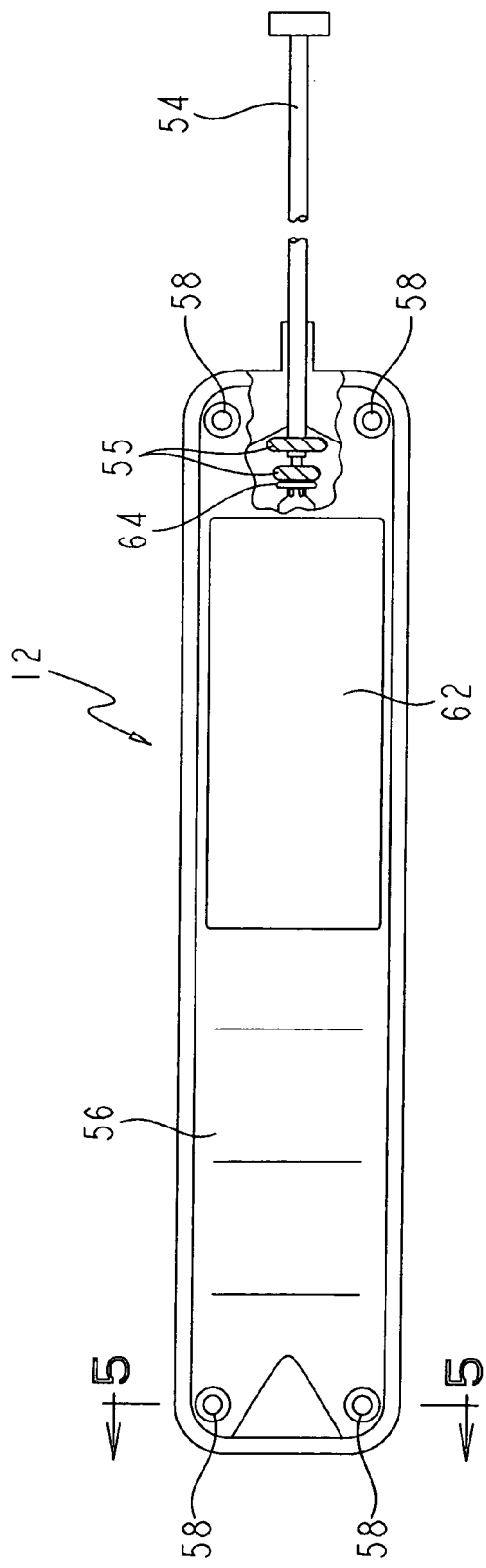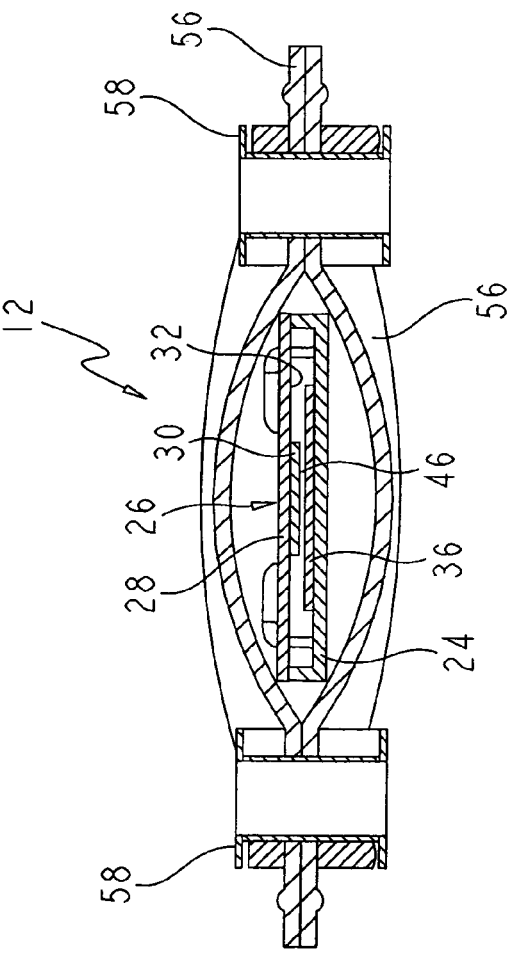

US 7,464,605 B2

BED HAVING A PATIENT POSITION MONITORING SYSTEM

CROSS-REFERENCE TO RELATED APPLICATIONS

This application claims the benefit of U.S. Provisional Patent Application Ser. No. 60/608,012, filed Sep. 8, 2004, titled BED HAVING A PATIENT POSITION MONITORING SYSTEM, the disclosure of which is expressly incorporated herein by reference.

BACKGROUND AND SUMMARY OF THE INVENTION

The present invention relates generally to a patient support and, more particularly, to a patient sensor for detecting the presence of a patient supported on a patient support surface.

According to an illustrative embodiment of the present disclosure, a patient sensor is configured to detect a force generated by a patient supported on a patient support surface, the patient sensor comprising a base, a detector operably coupled to the base and positioned below the patient support surface, wherein the detector is configured to detect a force applied to the patient support surface. A force collector extends outwardly from the base toward the detector and is configured to collect and concentrate the force applied to the patient support surface and to direct the force to the detector.

According to a further illustrative embodiment of the present disclosure, a patient sensor comprises a base, a force sensing resistor having a resistance value configured to change depending upon the amount of force applied thereto, and a shear reducing coupler operably coupling the base to the force sensing resistor such that at least portions of the force sensor resistor are free to move relative to the base.

According to yet another illustrative embodiment of the present disclosure, a patient sensor is configured to detect force exerted by a patient against a patient support surface, the patient sensor comprising a base, and a force sensing resistor operably coupled to the base, wherein the force sensing resistor has a resistance value configured to change depending upon the amount of force applied thereto. A spacer is supported by the base and is configured to position the base in spaced relation to the force sensing resistor.

Further illustratively, the force sensing resistor is operably coupled to a controller and includes a fault condition configured to be detected by the controller. Illustratively, a resistor is coupled intermediate the force sensing resistor and the controller for providing the fault condition.

Additional features and advantages of the present invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description of the drawings particularly refers to the accompanying figures in which:

FIG. 4 is a top plan view of the patient sensor of FIG. 3, with a partial cut-away thereof;

FIG. 5 is a cross-sectional view taken along line 5-5 of FIG. 4;

DETAILED DESCRIPTION OF THE DRAWINGS

Figure 1:
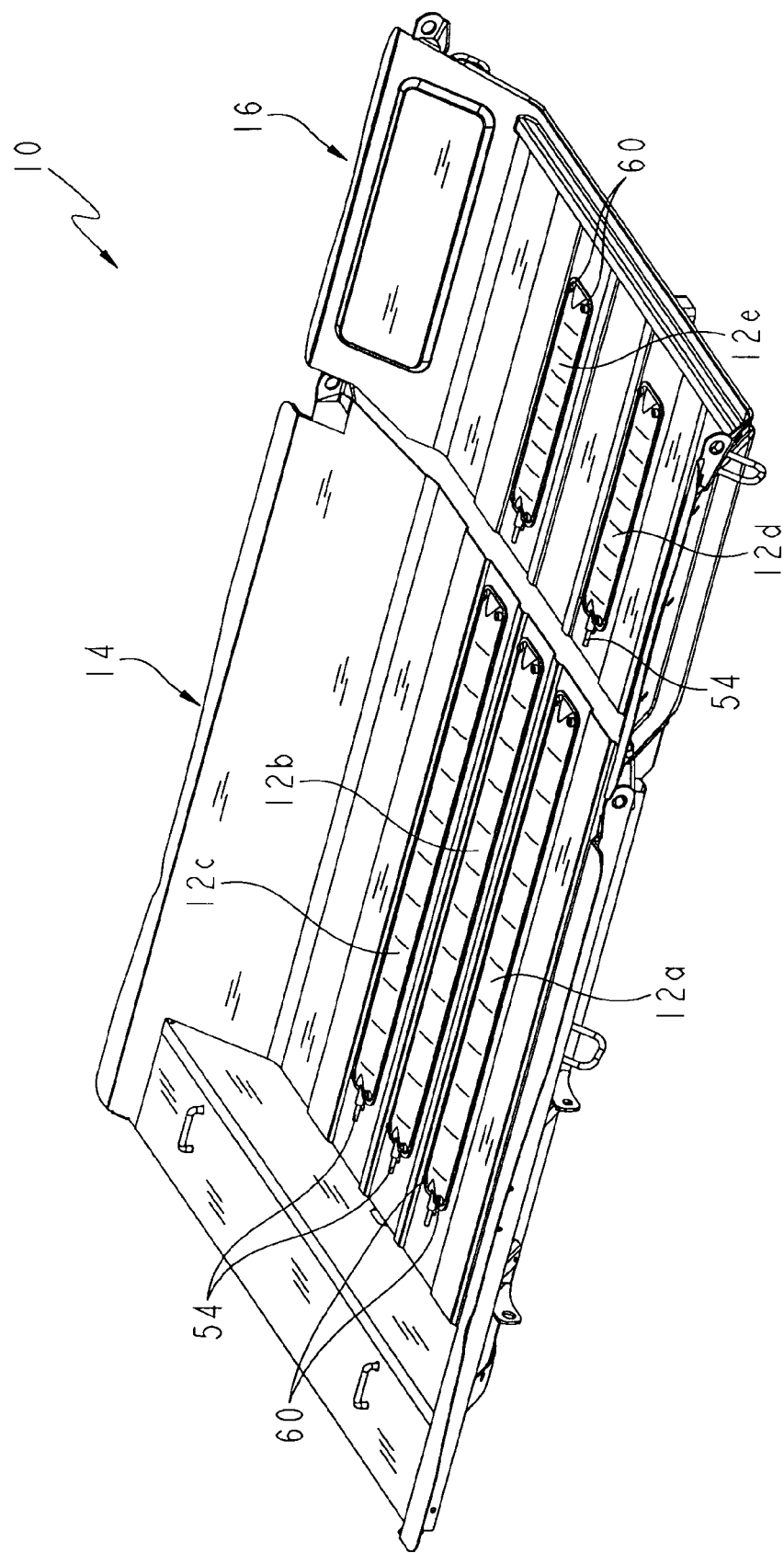
FIG. 1 is a perspective view of the head section and the seat section of an articulated support deck of a patient support, including a plurality of patient sensors according to an illustrative embodiment of the present disclosure.
Figure 2:
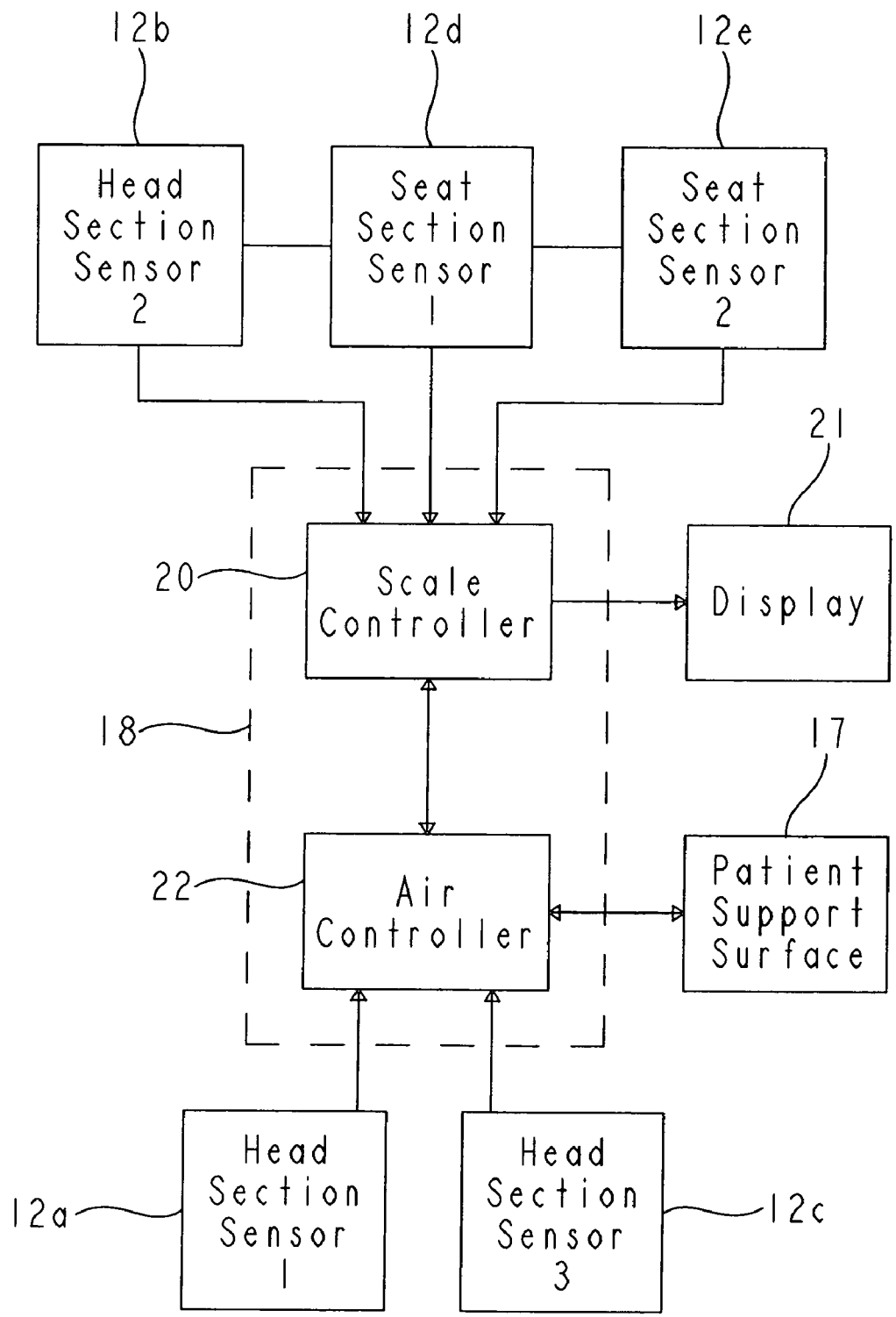
FIG. 2 is a block diagram illustrating interaction with an illustrative embodiment of the control system.
Figure 3:
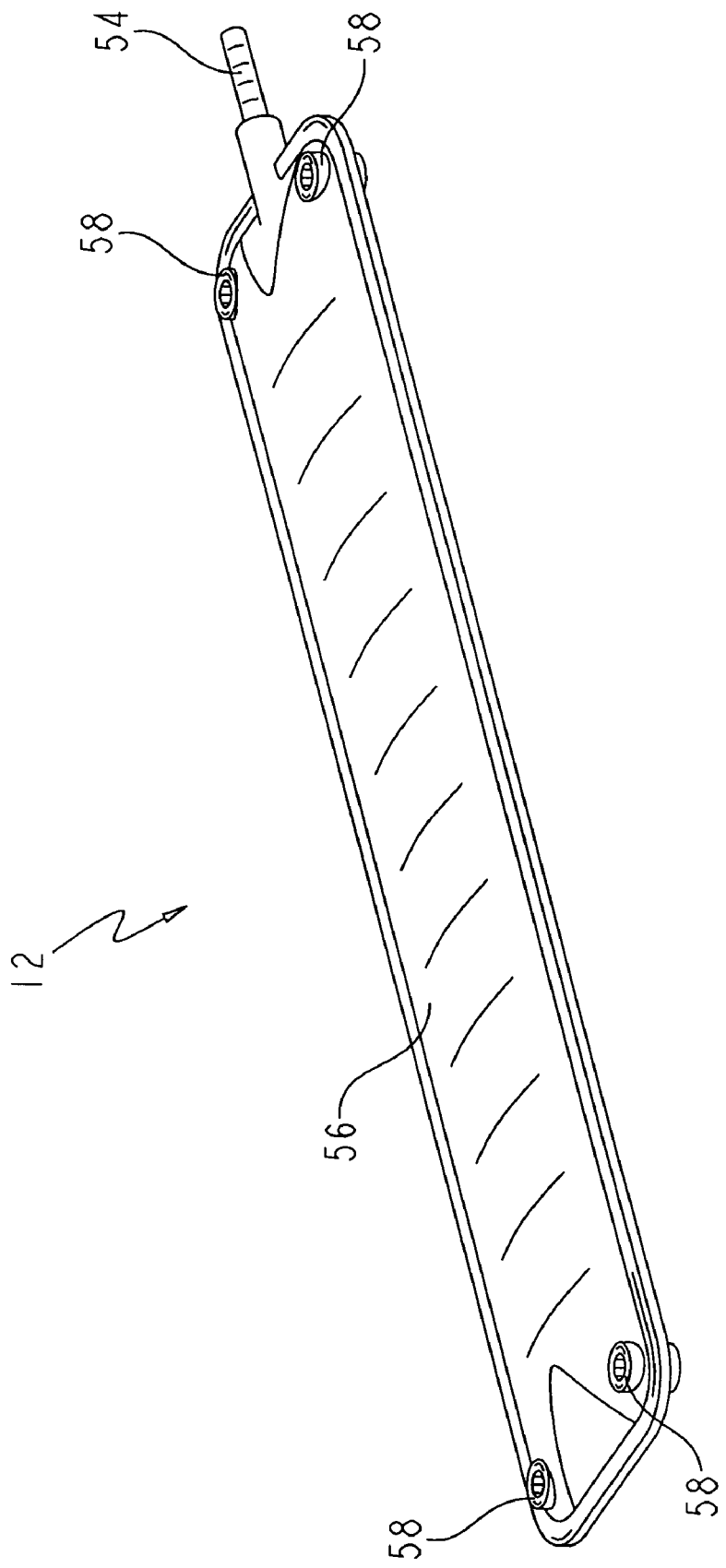
FIG. 3 is a perspective view of an illustrative embodiment patient sensor of FIG. 1.
Figure 6:
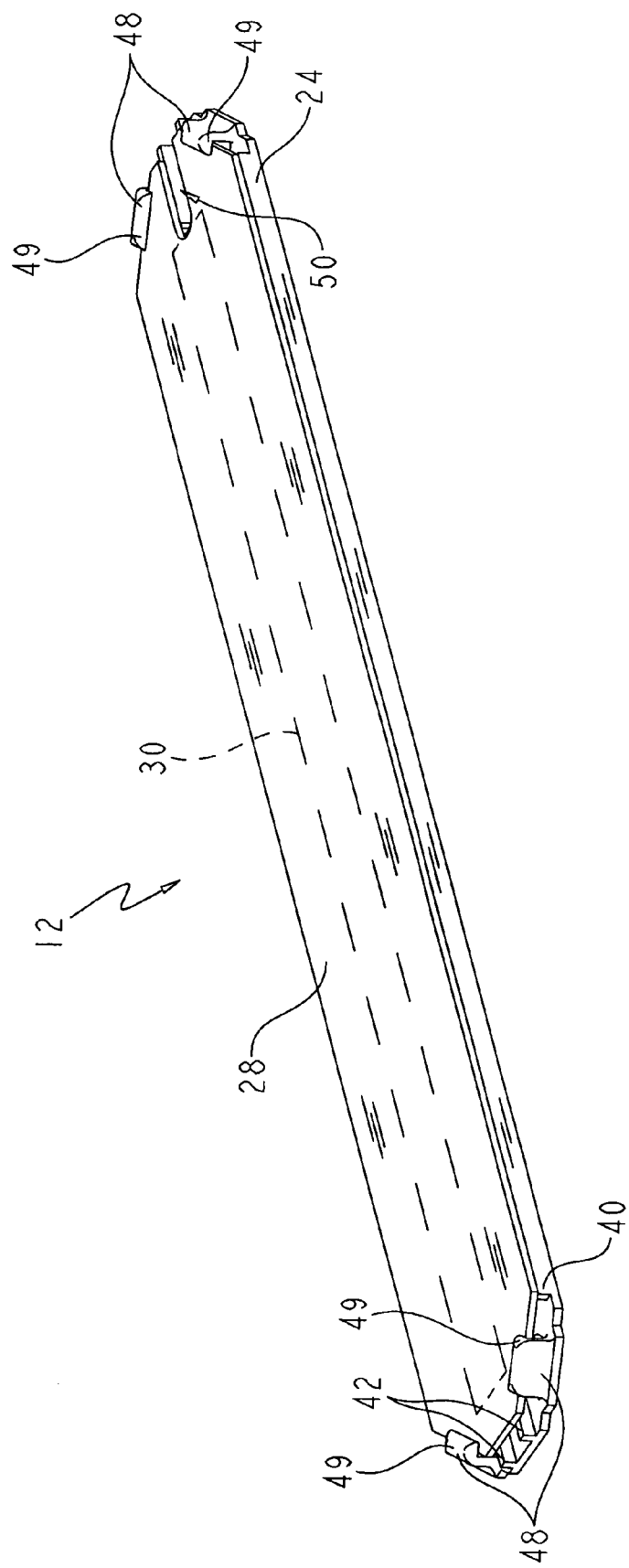
FIG. 6 is a perspective view illustrating the base operably coupled to a sensor assembly of the present disclosure.
Figure 7:
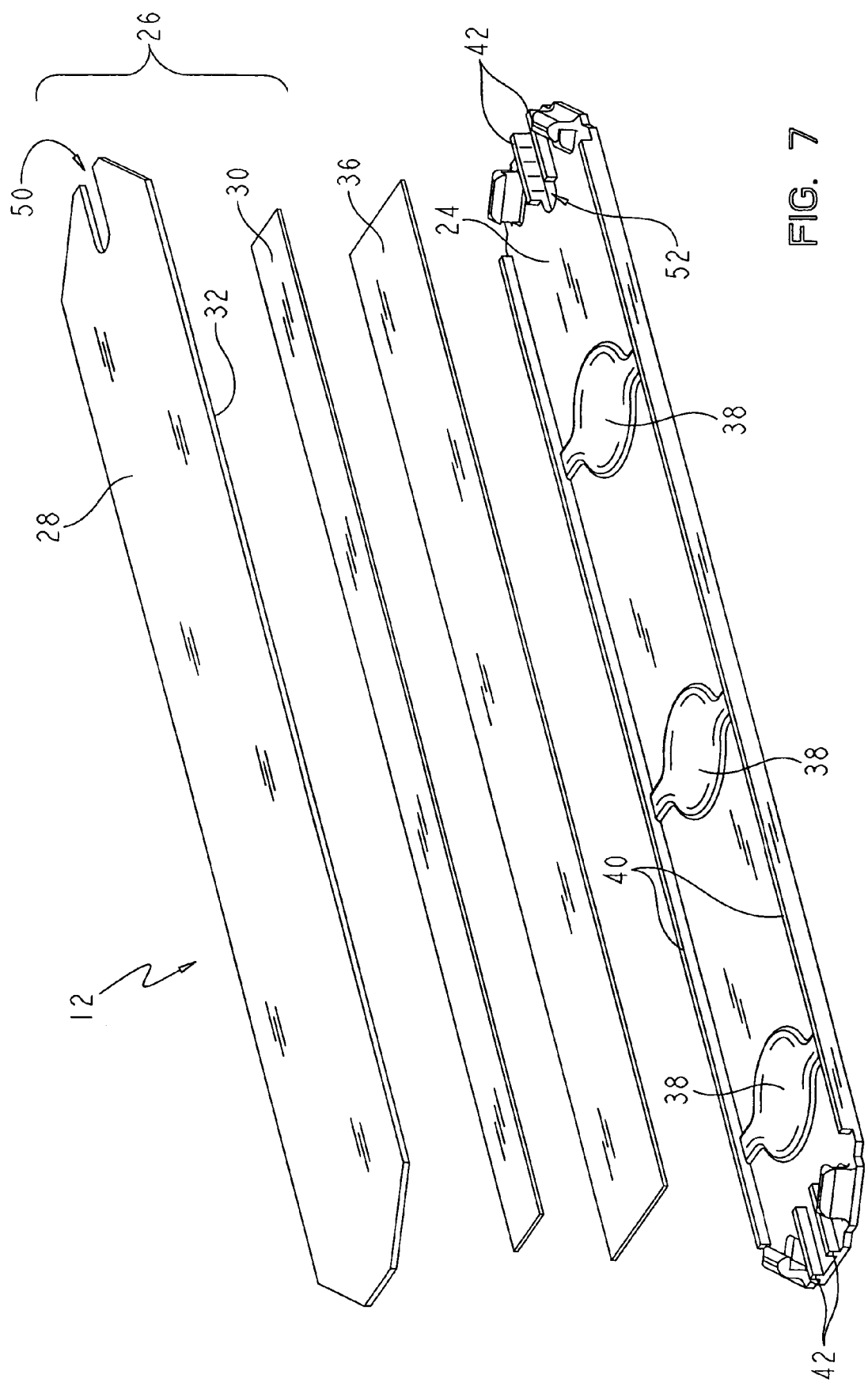
FIG. 7 is an exploded perspective view of the assembly of FIG. 6.

Referring initially to FIGS. 1 and 2, a patient support deck 10 is illustrated as including a plurality of patient sensors 12 according to an illustrative embodiment of the present disclosure. The patient support deck 10 may be of conventional design and illustratively includes an articulated head section 14, seat section 16, and foot section (not shown). The patient support deck 10 is configured to support a patient support surface 17, such as an air mattress. Additional details of an illustrative patient support deck 10 and patient support surface 17 are provided in U.S. patent application Ser. No. 10/657,696, filed Sep. 8, 2003, which is assigned to the assignee of the present invention and the disclosure of which is expressly incorporated by reference herein.

In the illustrative embodiment, there are a total of five patient sensors 12, including three sensors 12a, 12b, 12c supported by the head section 14 of the deck 10 and two patient sensors 12d, 12e supported by the seat section 16 of the deck 10. The patient sensors 12 are illustratively operably coupled to a control system 18. Illustratively, the control system 18 includes a scale controller 20 operably coupled to first and second seat section sensors 12d and 12e and second head section sensor 12b. The sensors 12b, 12d, 12e provide input to a patient position monitoring (PPM) system operated by the scale controller 20 and which is configured to notify a caregiver via a display 21 when the patient changes position relative to the patient support surface 17. The control system 18 may also include an air controller 22 in communication with the first head section sensor 12a and the third head section sensor 12c and configured to adjust the pressure within the patient support surface 17 in response to forces exerted by the patient against the patient sensors 12. As shown in FIG. 2, the scale controller 20 is in communication with the air controller 22 so that the sensors 12 may be configured to be in direct communication with the scale controller 20, the air controller 22, or some other controller of control system 18. Additional details regarding the operation of the scale controller 20 and the air controller 22 are provided in U.S. patent application Ser. No. 10/657,696, filed Sep. 8, 2003.

Referring now to FIGS. 3-7, each patient sensor 12 includes a base or compression plate 24 operably coupled to a detector assembly 26. The detector assembly 26 includes a backing plate or strip 28 and a detector 30 affixed to a lower surface 32 of the backing plate 28. The backing plate 28 may comprise a polyvinylchloride (PVC) or printed circuit board (PCB) G10 material. Illustratively, the detector 30 comprises a force sensing resistor (FSR) 34 in the form of an elongated strip. The force sensing resistor 34 is of conventional design and has a resistance value which changes depending upon the amount of force applied thereto. The force sensing resistor 34 illustratively comprises a polymer thick film (PTF) device which exhibits a decrease in resistance with an increase in the force applied to an active surface. More particularly, the resistance of the force sensing resistor 34 drops below a predetermined value when a certain force is applied. Illustrative force sensing resistors 34 are available from Interlink Electronics of Camarillo, Calif. and Recora Company of Batavia, Ill.

An elastic force distributor 36 is positioned intermediate the base 24 and the force sensing resistor 34. The elastic force distributor 36 is configured to distribute force applied to the patient support surface to the force sensing resistor 34. Illustratively, the elastic force distributor 36 comprises a urethane foam, such as PORON® available from Rogers Corporation of Woodstock, Conn.

Further illustratively, a plurality of spaced apart force collectors 38 extend upwardly from the base 24 and are configured to collect and concentrate the force applied to the patient support surface and to direct the force to the force sensing resistor 34. More particularly, the force collectors 38 of base 24 collect the force of the load and applies it to smaller areas of the FSR 34 which then are detectable. As such, the FSR 34 is capable of detecting smaller, lighter patients on the patient support surface 17 than without the base 24. In the illustrative embodiment, the detector assembly 26 is configured to detect a 50 lb. patient supported on the patient support surface 17. Illustratively, the force collectors 38 comprise a plurality of spaced apart disks integrally formed with the base 24. More particularly, the base 24 illustratively comprises a thermoplastic material molded to include force collectors 38 and a plurality of spacers 40, 42.

The plurality of upwardly extending spacers 40 and 42 are supported by the base 24 and are configured to position the base 24 in spaced relation to the force sensing resistor 34 and the elastic force distributor 36. The spacers illustratively include first and second longitudinally extending side rails 40 and first and second end rails 42. The backing plate 28 rests on the rails 40 and 42 and provide an air gap 46 between the force sensing resistor 34 and the force distributor 36 (FIG. 5). The spacers 40, 42 eliminate pre-loading on the detector assembly 26 due to weight of the patient support surface or mattress 17 and changes in patient support deck position. In order to prevent false detections of a patient, the spacers 40, 42 leave air gap 46 between the force sensing resistor 34 and the force distributor 36. As such, a force greater than the weight of the mattress 17 or as a result of deck position is required to activate the FSR 34. This enables the sensors 12 to work in a repeatable and consistent manner.

A plurality of sheer reducing couplers 48 operably couple the base 24 to the force sensing resistor 34. More particularly, the couplers 48 each includes a hook having an inwardly extending resilient arm 49 configured to retain the backing plate 28 intermediate the arm 49 and the rails 42 and 44. The couplers 48 provide for a "snap-fit" of the backing plate 28 to the base 24 at opposing ends thereof. The couplers 48 provide for limited relative movement of the backing plate 28 both laterally and longitudinally relative to the base 24. Further, the backing plate 28 intermediate the couplers 48 is not directly restrained. As such, the FSR 34 is resistant to shear forces developed between the patient support surface 17 and the support deck 10, thereby providing more reliable and consistent operation regardless of external criteria.

Slots 50 and 52 are provided in the backing plate 28 and the base 24 to provide access for a cable 54 (FIG. 7) in communication with the force sensing resistor 34. A strain relief 55 is coupled to the cable 54 and illustratively provides for a minimum force of 19 lbs. to disengage from the force sensing resistor 34. An outer cover 56 encapsulates the base 24 and sensor assembly 26. A plurality of eyelets 58 are coupled to the outer cover 56 and provide mounting points for the patient sensor 12. More particularly, the eyelets 58 may be secured to the patient support deck 10 through conventional fasteners 60, such as rivets. A label 62 may be attached to the outer cover 56 to provide information to the caregiver.

The patient sensors 12 are configured to generate a detection signal to the control system 18 only when a predetermined sufficient force is applied thereto or when a fault or disconnect condition occurs. As such, the patient sensors 12 are configured to avoid generating false detection signals which could impact normal operation of the patient support.

Each sensor 12 is configured to detect not only a force exerted by a patient, but also a sensor fault or disconnect condition. More particularly, each sensor 12 is configured to provide a logic high value to the control system 18 when a patient is not detected such that the sensor 12 has a resistance value above a predetermined amount, and a logic low value when a patient is detected such that the sensor has a resistance value equal to or below the predetermined amount. More particularly, the logic low value represents the interference detection signal to control system 18. A resistor 64, illustratively having a value of 34 kohms is coupled to the force sensing resistor 34 and provides a default logic high value. As such, if the sensor 12 is disconnected, a logic low value will result indicating a fault or disconnect of the sensor 12 to the control system 18.

Although the invention has been described in detail with reference to certain preferred embodiments, variations and modifications exist within the spirit and scope of the invention as described and defined in the following claims.

The invention claimed is:

1. A patient sensor configured to detect a force generated by a patient supported on a patient support surface, the patient sensor comprising:
   a base;
   a detector operably coupled to the base and positioned below the patient support surface, the detector being configured to detect a force applied to a patient support surface, wherein the detector comprises an elongated force sensing resistive strip; and
   a force collector including a plurality of members extending away from the base toward the detector, the force collector being configured to collect and concentrate the force applied to the patient support surface and to direct the force to predetermined areas of the force sensing resistive strip.

2. The patient sensor of claim 1, further comprising an outer cover surrounding the base, the detector, and the force collector.

3. The patient sensor of claim 1, wherein the detector comprises a force sensing resistor having a resistance value configured to change depending upon the amount of force applied thereto.

4. The patient sensor of claim 1, further comprising a backing plate supporting the detector.

5. The patient sensor of claim 4, further comprising shear reducing couplers operably coupling the base to the backing plate such that at least portions of the backing plate are free to move relative to the base.

6. The patient sensor of claim 4, further comprising a spacer supported by the base and configured to separate the base from the backing plate.

7. The patient sensor of claim 1, further comprising an elastic force distributor positioned intermediate the base and the detector, the elastic force distributor configured to distribute force applied to the patient support surface.

8. The patient sensor of claim 7, wherein the elastic force distributor comprises a polyurethane foam.

9. A patient sensor comprising:
   a base;

a force sensing resistor having a resistance value configured to change depending upon the amount of force applied thereto; and a shear reducing coupler operably coupling the base to the force sensing resistor such that at least portions of the force sensing resistor are free to move relative to the base, wherein the coupler comprises a plurality of hooks configured to releasably couple the force sensing resistor to the base.

10. The patient sensor of claim 9, wherein the plurality of hooks are positioned at opposing ends of the base.

11. The patient sensor of claim 9, further comprising a backing plate coupled to the force sensing resistor, the plurality of hooks each including an arm configured to retain the backing plate by providing a snap-fit.

12. The patient sensor of claim 9, further comprising a spacer supported by the base and configured to separate the base from the force sensing resistor.

13. The patient sensor of claim 9, further comprising an elastic force distributor positioned intermediate the base and the force sensing resistor, the elastic force distributor configured to distribute force applied to the patient support surface.

14. A patient sensor configured to detect force exerted by a patient against a patient support surface, the patient sensor comprising:
 a base;
 a flexible backing plate;
 a force sensing resistor operably coupled to the base, the force sensing resistor having a resistance value configured to change depending upon the amount of force applied thereto, the force sensing resistor being coupled to the flexible backing plate; and
 a spacer supported by the base and configured to engage longitudinal edge regions of the flexible backing plate to position the base in spaced relation to the force sensing resistor.

15. The patient sensor of claim 14, wherein the spacer includes first and second longitudinally extending side rail members extending upwardly from the base.

16. The patient sensor of claim 15, wherein the spacer further includes first and second end rail members extending upwardly from the base.

17. The patient sensor of claim 14, wherein the backing plate supports the force sensing resistor above raised areas of the base.

18. The patient sensor of claim 17, further comprising shear reducing couplers operably coupling the base to the backing plate.

19. The patient sensor of claim 14, further comprising an elastic force distributor positioned intermediate the base and the force sensing resistor, the elastic force distributor configured to distribute force applied to the patient support surface.

20. The patient sensor of claim 14, wherein the force sensing resistor is operably coupled to a controller and includes a fault condition configured to be detected by the controller.

21. The patient sensor of claim 20, wherein a resistor is coupled intermediate the force sensing resistor and the controller for providing the fault condition.

* * * * *